US008933097B2

(12) United States Patent
Chrzan et al.

(10) Patent No.: US 8,933,097 B2
(45) Date of Patent: Jan. 13, 2015

(54) FEXOFENADINE SUSPENSION FORMULATION

(75) Inventors: Kazimierz Chrzan, New Hope, PA (US); Rajiv Haribhakti, Churchville, PA (US); Matthew Mermey, Leawood, KS (US); Curtis J. Porcello, Ewing, NJ (US); Gary Lee Silvey, Overland Park, KS (US); Vinh Tran, Leawood, KS (US); Prafulla Agrawala, Kendall Park, NJ (US)

(73) Assignee: Sanofi-Aventis U.S. LLC, Bridgewater, NJ (US)

( * ) Notice: Subject to any disclaimer, the term of this patent is extended or adjusted under 35 U.S.C. 154(b) by 1525 days.

(21) Appl. No.: 12/138,468

(22) Filed: Jun. 13, 2008

(65) Prior Publication Data
US 2008/0299211 A1    Dec. 4, 2008

Related U.S. Application Data

(63) Continuation of application No. PCT/US2006/047393, filed on Dec. 12, 2006.

(60) Provisional application No. 60/750,303, filed on Dec. 14, 2005.

(51) Int. Cl.
*A01N 43/40* (2006.01)
*A61K 31/445* (2006.01)

(52) U.S. Cl.
USPC .......................................... 514/317; 514/319

(58) Field of Classification Search
USPC .......................................................... 514/317
See application file for complete search history.

(56) References Cited

U.S. PATENT DOCUMENTS

| | | | |
|---|---|---|---|
| 4,254,129 A | | 3/1981 | Carr et al. |
| 6,319,513 B1 * | | 11/2001 | Dobrozsi ........................ 424/434 |
| 2002/0193603 A1 | | 12/2002 | Henton et al. |
| 2005/0250737 A1 * | | 11/2005 | Hughes et al. ................... 514/58 |
| 2006/0083691 A1 * | | 4/2006 | Wermeling ....................... 424/45 |
| 2006/0110331 A1 * | | 5/2006 | Dang et al. ...................... 424/45 |

FOREIGN PATENT DOCUMENTS

| | | |
|---|---|---|
| CA | 1313136 C | 1/1993 |
| EP | 1 082 117 B1 | 1/2004 |
| WO | WO-00/21510 A2 | 4/2000 |
| WO | WO-00/21510 A3 | 4/2000 |
| WO | WO-03/011295 A1 | 2/2003 |
| WO | WO03/041683 | 5/2003 |
| WO | WO2004/066974 | 8/2004 |
| WO | WO-2005/115353 A1 | 12/2005 |
| WO | WO 2007/017095 | 2/2007 |

OTHER PUBLICATIONS

Tessler et al. (The methanol disolvate and the dihydrate of fexofenadine, an antihistamine drug. Acta Cryst. (2005).*
Grubbe et al., The Pharmacokinetics (PK), Safety and Tolerability of Fexofenadine HCl 6 mg/mL Suspension in Children with Allergic Rhinitis (AR): a Multicenter, Open-label, Single-dose Study, J. Allergy Clin. Immunol., vol. 119, No. 1 (Jan. 2007), p. S143, Abstract No. 563.
Morrison et al., The 30 mg Dose of Fexofenadine HCl 6 mg/mL Suspension is Bioequivalent to the Marketed 30 mg Tablet in Healthy Adult Subjects under Fasted Conditions: a Randomized, Crossover, Open-Label Study, J. Allergy Clin. Immunol., vol. 119, No. 1 (Jan. 2007), p. S143, Abstract No. 564.
Simpson et al., Fexofenadine: A Review of its Use in the Management of Seasonal Allergic Rhinitis and Chronic Idiopathic Urticaria, Drugs, ADIS International Ltd., vol. 2, No. 59 (Feb. 2000). pp. 301-321.
International Search Report for WO2007/070517 dated Jun. 21, 2007.
Chen, M.-L. et al. (Jan. 2007, e-pub. Oct. 18, 2006). "A Modern View of Excipient Effects on Bioequivalence: Case Study of Sorbitol," *Pharmaceutical Research* 24(1):73-80.
Hussain, A.S. et al. (2001). "Bioequivalence Evaluation of an Oral Solution of Metoprolol Containing Sorbitol," Meeting Abstract, *presented at the AAPS Annual Meeting and Exposition*, Colorado Convention Center, Denver, Oct. 21-25, 2001, as posted on http://abstracts.aaps.org/SecureView/AAPSJournal/0asn2jx9xaq873bmcpoe.htm, last visited on May 30, 2014, 1 page.
Li, B. et al. (Aug. 2005). "Effects of Sucrose and Mannitol on Asparagine Deamidation Rates of Model Peptides in Solution and in the Solid State," *Journal of Pharmaceutical Sciences* 94(8):1723-1735.
Prasanna, H.R. et al. (2001). "Linking Drug Substance Particle Size Specifications to Drug Product Dissolution," Meeting Abstract, *presented at the AAPS Annual Meeting and Exposition*, Colorado Convention Center, Denver, Oct. 21-25, 2001, as posted on http://abstracts.aaps.org/SecureView/AAPSJournal/p9l2kr3dthlj23qgvxxy.htm, last visited on May 30, 2014, 1 page.
Yu, L.X. et al. (2001). "Predicting Human Oral Bioavailability: Application to 26 Recently Approve Drugs," Meeting Abstract, *presented at the AAPS Annual Meeting and Exposition*, Colorado Convention Center, Denver, Oct. 21-25, 2001, as posted on http://abstracts.aaps.org/SecureView/AAPSJournal/h7pnj3uzxr90e01hn1d0.htm, last visited on May 30, 2014, 1 page.
Costa Rica Office Action dated Mar. 11, 2014 for Costa Rican Patent Application No. 9993, filed Dec. 12, 2006, 13 pages. (English Translation).

* cited by examiner

*Primary Examiner* — Layla Soroush
(74) *Attorney, Agent, or Firm* — Morrison & Foerster LLP

(57) ABSTRACT

The present invention is directed to an aqueous pharmaceutical suspension of fexofenadine zwitterionic dihydrate Form I.

88 Claims, 4 Drawing Sheets

Figure 1 – SSNMR Experiment of Manufacturing Step; Fexofenadine HCl Addition During Manufacturing Process Figure 2 – XRPD of Manufacturing Step: Fexofenadine HCl Addition During Manufacturing Process Figure 3 - FTIR Spectrum of Fexofenadine Hydrochloride Anhydrous Form I Figure 4 - FTIR Spectrum of Fexofenadine Zwitterionic Dihydrate Form I

US 8,933,097 B2

FEXOFENADINE SUSPENSION FORMULATION

This application is a Continuation of International Application No. PCT/US2006/047393, filed Dec. 12, 2006, which claims the benefit of U.S. Provisional Application No. 60/750,303, filed Dec. 14, 2005.

FIELD OF THE INVENTION

This invention is directed to an aqueous suspension formulation of fexofenadine zwitterionic dihydrate Form I.

BACKGROUND OF THE INVENTION

Fexofenadine and its pharmaceutically acceptable salts are useful as antihistamines as disclosed in U.S. Pat. No. 4,254,129 and U.S. Publication No. 2002-0193603 A1. Fexofenadine hydrochloride is available commercially in a variety of solid dosage forms including immediate-release capsules, immediate-release tablets, and sustained-release tablets. There is no disclosure, however, as to an aqueous suspension formulation of fexofenadine or a zwitterionic dihydrate crystalline form of fexofenadine. Neither is there disclosure regarding any suspension formulation as being particularly suitable for ease of dosing children, or for dosing adults having problems with swallowing capsules and tablets, as the suspension formulation according to the present invention would be.

SUMMARY OF THE INVENTION

The present invention is directed to an aqueous pharmaceutical suspension, buffered to a pH about 4.25 to about 9.43, comprising, by weight/volume (g/100 mL), about 0.03% to about 4.80% of fexofenadine zwitterionic dihydrate Form I of formula (I) having a particle size of less than about 280 μm for at least about 90% of the fexofenadine zwitterionic dihydrate Form I;

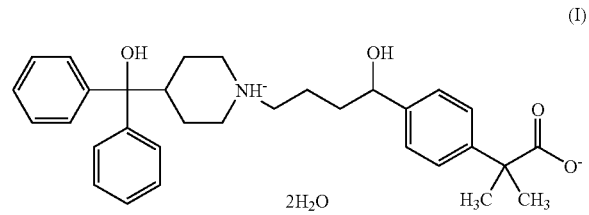

(I)

about 0.01% to about 0.20% of a wetting agent;
a suspending agent selected from about 0.10% to about 0.50% of a hydrocolloid gum, or about 0.1% to about 1.0% of hydroxyethylcellulose;
a sweetener system comprising
about 5% to about 40% of sucrose or invert sucrose; and
0% to about 40% of xylitol, sorbitol or sorbitol solution, or maltitol solution;
provided that the ratio of the amount of (sucrose or invert sucrose):(xylitol, sorbitol or sorbitol solution, or maltitol solution) is equal or greater than about 1:1; and
a preservative system comprising
about 0.010% to about 0.058% of propylparaben, sodium propylparaben or potassium propylparaben; and
about 0.0005% to about 0.0350% of butylparaben or sodium butylparaben.

The present invention is more fully discussed with the aid of the following figures and detailed description below.

DETAILED DESCRIPTION OF THE INVENTION

Definition of Terms

Figure 1:
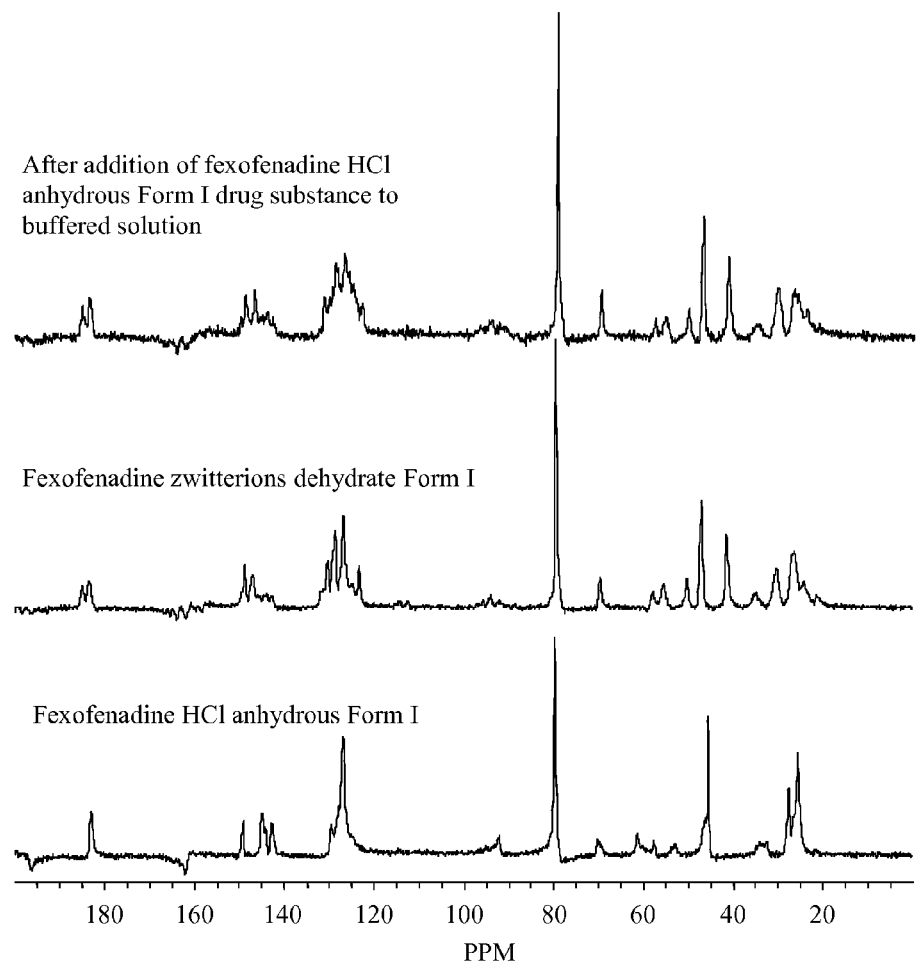
FIG. 1 is Solid State NMR spectra of the suspended fexofenadine collected after addition of fexofenadine hydrochloride anhydrous Form I to the buffered solution during the manufacturing process, fexofenadine hydrochloride anhydrous Form I, and fexofenadine zwitterionic dihydrate Form I.

As used above, and throughout the description of the invention, the following terms, unless otherwise indicated, shall be understood to have the following meanings.

"A corresponding equivalent amount of potassium phosphate dibasic hydrate" means an amount of a hydrated form of potassium phosphate dibasic that is equivalent to the corresponding required amount of potassium phosphate dibasic for adjusting the pH of the suspension.

"90% CI" means 90% confidence interval.

"A corresponding equivalent amount of sodium phosphate monobasic hydrate" means an amount of a hydrated form of sodium phosphate monobasic that is equivalent to the corresponding required amount of sodium phosphate monobasic for adjusting the pH of the suspension.

"A corresponding equivalent amount of sodium phosphate dibasic hydrate" means an amount of a hydrated form of sodium phosphate dibasic that is equivalent to the corresponding required amount of sodium phosphate dibasic for adjusting the pH of the suspension.

"AUC(0-∞)" means area under the plasma concentration time curve extrapolated to infinity.

"Cmax" means maximum plasma concentration.

"Buffer system" is used to adjust the pH of the suspension to minimize the solubility of the constituent fexofenadine and to maintain that fexofenadine as fexofenadine zwitterionic dihydrate Form I for a minimum of about 18 months; more particularly for at least about 24 months. Examples of the buffer system include (citric acid/sodium phosphate dibasic or sodium phosphate dibasic hydrate) system, (succinic acid/sodium hydroxide) system, (citric acid/sodium citrate, sodium citrate hydrate or potassium citrate) system, (maleic acid/sodium hydroxide) system, (fumaric acid/sodium hydroxide) system, (sodium phosphate monobasic, sodium phosphate monobasic hydrate or potassium phosphate monobasic/sodium phosphate dibasic, sodium phosphate dibasic hydrate, potassium phosphate dibasic or potassium phosphate dibasic hydrate) system, particularly (sodium phosphate monobasic, sodium phosphate monobasic hydrate or potassium phosphate monobasic/sodium phosphate dibasic, sodium phosphate dibasic hydrate, potassium phosphate dibasic or potassium phosphate dibasic hydrate) system, more particularly (sodium phosphate monobasic, or sodium phosphate monobasic hydrate/sodium phosphate dibasic, or sodium phosphate dibasic hydrate) system, even more particularly (sodium phosphate monobasic monohydrate/sodium phosphate dibasic heptahydrate) system.

"CV %" means coefficient of variation.

"Geometric LS Mean" means geometric least squares mean.

"Maltitol solution" is an aqueous solution of a hydrogenated, partially hydrolyzed starch, containing more than about 50% w/w of D-maltitol ($C_{12}H_{24}O_{11}$), and normally more than 90% w/w of D-maltitol and less than about 16% w/w of D-sorbitol ($C_6H_{14}O_6$). It is also known as hydrogenated glucose syrup (generic term). It generally contains D-maltitol, along with D-sorbitol and hydrogenated oligo- and polysaccharides.

"Particle size" is determined utilizing Low-Angle Laser Light-Scattering (LALLS), and is calculated as spheres of equivalent diameter to the test sample. Particle size distribution is described as the volume % above or below the stated diameter. For example the $Dv_{10}$, $Dv_{50}$ and $Dv_{90}$ correspond, respectively, to the particle diameter as which 10, 50 and 90% of the total particle size distribution volume is below the stated diameter.

"Poloxamer" is $\alpha$-Hydro-$\omega$-hydroxypoly(oxyethylene) poly(oxypropylene) poly(oxyethylene) block copolymer. Examples of Poloxamer include Poloxamer 407 and Poloxamer 188.

"Potassium phosphate monobasic" means $KH_2PO_4$.

"Potassium phosphate dibasic" means $K_2HPO_4$.

"Potassium phosphate dibasic hydrate" includes, for example, potassium phosphate dibasic trihydrate and potassium phosphate dibasic hexahydrate.

"Sodium phosphate monobasic" means $NaH_2PO_4$.

"Sodium phosphate monobasic hydrate" includes, for example, sodium phosphate monobasic monohydrate, and sodium phosphate monobasic dihydrate.

"Sodium phosphate dibasic" means $Na_2HPO_4$.

"Sodium phosphate dibasic hydrate" includes, for example, sodium phosphate dibasic dihydrate, sodium phosphate dibasic heptahydrate, and sodium phosphate dibasic dodecahydrate.

"Sorbitol solution" includes sorbitol solution USP and sorbitol solution noncrystallizing NF, as defined by U.S. Pharmacopoeia. Sorbitol Solution USP is an aqueous solution comprising not less than 64% D-sorbitol (normally labeled as 70%). Sorbitol solution noncrystallizing NF is an aqueous solution comprising not less than 45% D-sorbitol.

Particular Embodiments of The Invention

With reference to the present invention described herein, below are particular embodiments related thereto.

One particular embodiment of the invention is the aqueous pharmaceutical suspension, wherein the preservative system further comprises about 0.06% to about 0.26% of edetate disodium, about 0.01% to about 0.27% of benzoic acid or sodium benzoate, about 0.01% to about 0.30% of sorbic acid or potassium sorbate or about 0.10% to about 1.50% of benzyl alcohol.

Another particular embodiment of the invention is the aqueous pharmaceutical suspension, wherein the pH is about 5.00 to about 8.00; or more particularly 5.80 to about 7.00.

Another particular embodiment of the invention is the aqueous pharmaceutical suspension, wherein the particle size is less than about 50 μm; or more particularly 40 μm; for at least about 90% of the fexofenadine zwitterionic dihydrate Form I.

Another particular embodiment of the invention is the aqueous pharmaceutical suspension, wherein the fexofenadine zwitterionic dihydrate Form I is, by weight/volume (g/100 mL), about 0.60% to about 1.20%; more particularly about 0.6%.

Another particular embodiment of the invention is the aqueous pharmaceutical suspension, wherein the wetting agent is, by weight/volume (g/100 mL), about 0.01% to about 0.05%; more particularly about 0.02% to about 0.05%.

Another particular embodiment of the invention is the aqueous pharmaceutical suspension, wherein the hydrocolloid gum is, by weight/volume (g/100 mL), about 0.23% to about 0.45%; more particularly about 0.35% to about 0.45%.

Another particular embodiment of the invention is the aqueous pharmaceutical suspension, wherein the hydrocolloid gum is xanthan gum.

Another particular embodiment of the invention is the aqueous pharmaceutical suspension, wherein the hydroxyethylcellulose is, by weight/volume (g/100 mL), about 0.2% to about 0.4%; or more particularly about 0.2% to about 0.3%.

Another particular embodiment of the invention is the aqueous pharmaceutical suspension, wherein xylitol, sorbitol or sorbitol solution, or maltitol solution is, by weight/volume (g/100 mL), 0% to about 20%; more particularly about 10% to about 20%; or further more particularly about 10%.

Another particular embodiment of the invention is the aqueous pharmaceutical suspension, wherein sucrose or invert sucrose is, by weight/volume (g/100 mL), about 10% to about 40%; more particularly about 10% to about 20%; or further more particularly about 20%.

Another particular embodiment of the invention is the aqueous pharmaceutical suspension, wherein the sweetener system comprises xylitol and sucrose.

Another particular embodiment of the invention is the aqueous pharmaceutical suspension, wherein the sweetener system comprises xylitol and sucrose, and the ratio of the amount of sucrose:xylitol is about 2:1.

Another particular embodiment of the invention is the aqueous pharmaceutical suspension, wherein the sweetener system comprises, by weight/volume (g/100 mL), 0% to about 20% of xylitol, and about 10% to about 40% of sucrose.

Another particular embodiment of the invention is the aqueous pharmaceutical suspension, wherein the sweetener system comprises, by weight/volume (g/100 mL), about 10% to about 20% of xylitol, and 10% to about 20% of sucrose.

Another particular embodiment of the invention is the aqueous pharmaceutical suspension, wherein the sweetener system comprises, by weight/volume (g/100 mL), about 20% of sucrose, and about 10% of xylitol.

Another particular embodiment of the invention is the aqueous pharmaceutical suspension, wherein the ratio of the amount of (sucrose or invert sucrose):(xylitol, sorbitol or sorbitol solution, or maltitol solution) is about 1:1 to 2:1.

Another particular embodiment of the invention is the aqueous pharmaceutical suspension, wherein the ratio of the amount of (sucrose or invert sucrose):(xylitol, sorbitol or sorbitol solution, or maltitol solution) is about 2:1.

Another particular embodiment of the invention is the aqueous pharmaceutical suspension, wherein the ratio of the amount of (sucrose or invert sucrose):(xylitol, sorbitol or sorbitol solution, or maltitol solution) is about 1:1.

Another particular embodiment of the invention is the aqueous pharmaceutical suspension, wherein the propylparaben, sodium propylparaben, or potassium propylparaben is, by weight/volume (g/100 mL), about 0.014% to about 0.048%; more particularly 0.027% to about 0.04%.

Another particular embodiment of the invention is the aqueous pharmaceutical suspension, wherein the butylparaben or sodium butylparaben is, by weight/volume (g/100 mL), about 0.0008% to about 0.0240%; more particularly about 0.014% to about 0.020%.

Another particular embodiment of the invention is the aqueous pharmaceutical suspension, wherein the edetate disodium is, by weight/volume (g/100 mL), about 0.10% to about 0.18%, particularly about 0.12% to about 0.18%.

Another particular embodiment of the invention is the aqueous pharmaceutical suspension, wherein the preservative system comprises propylparaben, butylparaben and edetate disodium.

Another particular embodiment of the invention is the aqueous pharmaceutical suspension, wherein the benzoic acid or sodium benzoate is, by weight/volume (g/100 mL), about 0.10% to about 0.20%; more particularly about 0.12% to about 0.18%.

Another particular embodiment of the invention is the aqueous pharmaceutical suspension, wherein the sorbic acid or potassium sorbate is, by weight/volume (g/100 mL), about 0.10% to about 0.22%; more particularly about 0.12% to about 0.20%.

Another particular embodiment of the invention is the aqueous pharmaceutical suspension, wherein the benzyl alcohol is, by weight/volume (g/100 mL), about 0.25% to about 1.00%; more particularly about 0.25% to about 0.50%.

Another particular embodiment of the invention is the aqueous pharmaceutical suspension, wherein the buffering uses a buffer system comprising, by weight/volume (g/100 mL),
    about 0.06% to about 1.05% of sodium phosphate monobasic or corresponding equivalent amount of a sodium phosphate monobasic hydrate, or about 0.069% to about 1.190% of potassium phosphate monobasic; and
    about 0.32% to about 2.69% of sodium phosphate dibasic or corresponding equivalent amount of a sodium phosphate dibasic hydrate, or about 0.39% to about 3.30% of potassium phosphate dibasic or corresponding equivalent amount of a potassium phosphate dibasic hydrate.

Another particular embodiment of the invention is the aqueous pharmaceutical suspension, wherein the buffering uses a buffer system comprising, by weight/volume (g/100 mL),
    about 0.22% to about 0.87% of sodium phosphate monobasic or a corresponding equivalent amount of a sodium phosphate monobasic hydrate, or about 0.25% to about 0.99% of potassium phosphate monobasic; and
    about 0.32% to about 1.15% of sodium phosphate dibasic or a corresponding equivalent amount of sodium phosphate dibasic hydrate, or about 0.39% to about 1.41% of potassium phosphate dibasic or a corresponding equivalent amount of potassium phosphate dibasic hydrate.

Another particular embodiment of the invention is the aqueous pharmaceutical suspension, wherein the buffering uses a buffer system comprising, by weight/volume (g/100 mL),
    about 0.65% to about 0.87% of sodium phosphate monobasic or a corresponding amount of a sodium phosphate monobasic hydrate, or about 0.74% to about 0.99% of potassium phosphate monobasic; and
    about 0.32% to about 0.67% of sodium phosphate dibasic or a corresponding equivalent amount of a sodium phosphate dibasic hydrate, or about 0.39% to about 0.82% of potassium phosphate dibasic or a corresponding amount of potassium phosphate dibasic hydrate.

Another particular embodiment of the invention is the aqueous pharmaceutical suspension, wherein the buffering uses a buffer system comprising, by weight/volume (g/100 mL),
    about 0.06% to about 1.05% of sodium phosphate monobasic or a corresponding equivalent amount of a sodium phosphate monobasic hydrate; and
    about 0.32% to about 2.69% of sodium phosphate dibasic or a corresponding amount of a sodium phosphate dibasic hydrate.

Another particular embodiment of the invention is the aqueous pharmaceutical suspension, wherein the buffering uses a buffer system comprising, by weight/volume (g/100 mL),
    about 0.22% to about 0.87% of sodium phosphate monobasic or a corresponding equivalent amount of a sodium phosphate monobasic hydrate; and
    about 0.32% to about 1.15% of sodium phosphate dibasic or a corresponding equivalent amount of a sodium phosphate dibasic hydrate.

Another particular embodiment of the invention is the aqueous pharmaceutical suspension, wherein the buffering uses a buffer system comprising, by weight/volume (g/100 mL),
    about 0.65% to about 0.87% of sodium phosphate monobasic or a corresponding equivalent amount of a sodium phosphate monobasic hydrate; and
    about 0.32% to about 0.67% of sodium phosphate dibasic or a corresponding equivalent amount of a sodium phosphate dibasic hydrate.

Another particular embodiment of the invention is the aqueous pharmaceutical suspension, wherein the buffering uses a buffer system comprising, by weight/volume (g/100 mL), about 0.07% to about 1.20% of sodium phosphate monobasic monohydrate, and about 0.60% to about 5.08% of sodium phosphate dibasic heptahydrate.

Another particular embodiment of the invention is the aqueous pharmaceutical suspension, wherein the buffering uses a buffer system comprising, by weight/volume (g/100 mL), about 0.26% to about 1.00% of sodium phosphate monobasic monohydrate, and about 0.60% to about 2.17% of sodium phosphate dibasic heptahydrate.

Another particular embodiment of the invention is the aqueous pharmaceutical suspension, wherein the buffering uses a buffer system comprising, by weight/volume (g/100 mL), about 0.75% to about 1.00% of sodium phosphate monobasic monohydrate, and about 0.60% to about 1.25% of sodium phosphate dibasic heptahydrate.

Another particular embodiment of the invention is the aqueous pharmaceutical suspension, wherein the wetting agent is nonionic, such as Poloxamer 407 and Poloxamer 188.

Another particular embodiment of the invention is the aqueous pharmaceutical suspension, optionally further comprising, by weight/volume (g/100 mL), about 0.1% to about 3.0%; more particularly about 1.0% to about 2.0%; or further more particularly about 1.5% to about 2.0% of microcrystalline cellulose.

Another particular embodiment of the invention is the aqueous pharmaceutical suspension, optionally further comprising, by weight/volume (g/100 mL), about 0.01% to about 0.20%; more particularly about 0.012% to about 0.13%; or further more particularly about 0.05% to about 0.10% of saccharin.

Another particular embodiment of the invention is the aqueous pharmaceutical suspension, optionally further comprising, by weight/volume (g/100 mL), about 0.01% to about 1.00%; more particularly about 0.01% to about 0.50%; or further more particularly about 0.01% to about 0.10% of acesulfame potassium or sucralose.

Another particular embodiment of the invention is the aqueous pharmaceutical suspension, optionally further comprising, by weight/volume (g/100 mL), about 0.1% to about 15.0%; more particularly about 1.0% to about 10.0%; or further more particularly about 2.5% to about 5.0% of a co-solvent, such as propylene glycol.

Another particular embodiment of the invention is the aqueous pharmaceutical suspension, optionally further comprising, by weight/volume (g/100 mL), 0% to about 4%; more particularly 0% to about 2%; or further more particularly 0% to about 1% of a co-solvent, such as polyethylene glycol 200, polyethylene glycol 300 or polyethylene glycol 400.

Another particular embodiment of the invention is the aqueous pharmaceutical suspension, optionally further comprising, by weight/volume (g/100 mL), 0% to about 0.50%; more particularly 0% to about 0.10%; or further more particularly about 0.05% to about 0.10% of an opacifying agent, such as titanium dioxide.

Another particular embodiment of the invention is the aqueous pharmaceutical suspension, optionally further comprising, by weight/volume (g/100 mL), about 0.20% to about 0.70%; more particularly about 0.30% to about 0.45%; or further more particularly about 0.40% to about 0.45% of a flavoring agent, such as artificial raspberry cream flavor or artificial orange cream flavor.

Another particular embodiment of the invention is the aqueous pharmaceutical suspension, buffered to a pH about 5.80 to about 7.00, comprising, by weight/volume (g/100 mL), about 0.60% of fexofenadine zwitterionic dihydrate Form I having a particle size of less than about 40 µm for at least about 90% of the fexofenadine zwitterionic dihydrate Form I, about 2.5% of propylene glycol, about 0.15% of edetate disodium, about 0.034% of propylparaben, about 0.017% of butylparaben, about 0.35% of xanthan gum, about 0.05% of Poloxamer 407, about 1.25% of sodium phosphate dibasic heptahydrate, about 0.75% of sodium phosphate monobasic monohydrate, about 20% of sucrose, and about 10% of xylitol.

Another particular embodiment of the invention is the aqueous pharmaceutical suspension, buffered to a pH about 5.80 to about 7.00, comprising, by weight/volume (g/100 mL), about 0.60% of fexofenadine zwitterionic dihydrate Form I having a particle size of less than about 40 µm for at least about 90% of the fexofenadine zwitterionic dihydrate Form I, about 2.5% of propylene glycol, about 0.15% of edetate disodium, about 0.034% of propylparaben, about 0.017% of butylparaben, about 0.35% of xanthan gum, about 0.05% of Poloxamer 407, about 1.25% of sodium phosphate dibasic heptahydrate, about 0.75% of sodium phosphate monobasic monohydrate, about 20% of sucrose, about 10% of xylitol, and about 0.1% of titanium dioxide.

Another particular embodiment of the invention is the aqueous pharmaceutical suspension, buffered to a pH about 5.80 to about 7.00, comprising, by weight/volume (g/100 mL), about 0.60% of fexofenadine zwitterionic dihydrate Form I having a particle size of less than about 40 µm for at least about 90% of the fexofenadine zwitterionic dihydrate Form I, about 2.5% of propylene glycol, about 0.15% of edetate disodium, about 0.034% of propylparaben, about 0.017% of butylparaben, about 0.35% of xanthan gum, about 0.05% of Poloxamer 407, about 1.25% of sodium phosphate dibasic heptahydrate, about 0.75% of sodium phosphate monobasic monohydrate, about 20% of sucrose, about 10% of xylitol, about 0.1% of titanium dioxide, and about 0.4% of raspberry cream flavor.

Another particular embodiment of the invention is the aqueous pharmaceutical suspension, buffered to a pH about 5.80 to about 7.00, comprising, by weight/volume (g/100 mL), about 0.60% of fexofenadine zwitterionic dihydrate Form I having a particle size of less than about 40 µm for at least about 90% of the fexofenadine zwitterionic dihydrate Form I, about 2.5% of propylene glycol, about 0.15% of edetate disodium, about 0.034% of propylparaben, about 0.017% of butylparaben, about 0.35% of xanthan gum, about 0.05% of Poloxamer 407, about 1.25% of sodium phosphate dibasic heptahydrate, about 0.75% of sodium phosphate monobasic monohydrate, about 10% of sucrose, and about 10% of xylitol.

Another particular embodiment of the invention is the aqueous pharmaceutical suspension, buffered to a pH about 5.80 to about 7.00, comprising, by weight/volume (g/100 mL), about 0.60% of fexofenadine zwitterionic dihydrate Form I having a particle size of less than about 40 µm for at least about 90% of the fexofenadine zwitterionic dihydrate Form I, about 2.5% of propylene glycol, about 0.15% of edetate disodium, about 0.034% of propylparaben, about 0.017% of butylparaben, about 0.35% of xanthan gum, about 0.05% of Poloxamer 407, about 1.25% of sodium phosphate dibasic heptahydrate, about 0.75% of sodium phosphate monobasic monohydrate, about 10% of sucrose, about 10% of xylitol, and about 0.1% of titanium dioxide.

Another particular embodiment of the invention is the aqueous pharmaceutical suspension, buffered to a pH about 5.80 to about 7.00, comprising, by weight/volume (g/100 mL), about 0.60% of fexofenadine zwitterionic dihydrate Form I having a particle size of less than about 40 µm for at least about 90% of the fexofenadine zwitterionic dihydrate Form I, about 2.5% of propylene glycol, about 0.15% of edetate disodium, about 0.034% of propylparaben, about 0.017% of butylparaben, about 0.35% of xanthan gum, about 0.05% of Poloxamer 407, about 1.25% of sodium phosphate dibasic heptahydrate, about 0.75% of sodium phosphate monobasic monohydrate, about 10% of sucrose, about 10% of xylitol, about 0.1% of titanium dioxide, and about 0.4% of raspberry cream flavor.

Another particular embodiment of the invention is the aqueous pharmaceutical suspension, buffered to a pH about 5.80 to about 7.00, comprising, by weight/volume (g/100 mL), about 0.60% of fexofenadine zwitterionic dihydrate Form I having a particle size of less than about 40 µm for at least about 90% of the fexofenadine zwitterionic dihydrate Form I, about 2.5% of propylene glycol, about 0.15% of edetate disodium, about 0.034% of propylparaben, about 0.017% of butylparaben, about 0.35% of xanthan gum, about 0.05% of Poloxamer 407, about 1.25% of sodium phosphate dibasic heptahydrate, about 0.75% of sodium phosphate monobasic monohydrate, about 20% of sucrose, and about 10% of sorbitol solution.

Another particular embodiment of the invention is the aqueous pharmaceutical suspension, buffered to a pH about 5.80 to about 7.00, comprising, by weight/volume (g/100 mL), about 0.60% of fexofenadine zwitterionic dihydrate Form I having a particle size of less than about 40 µm for at least about 90% of the fexofenadine zwitterionic dihydrate Form I, about 2.5% of propylene glycol, about 0.15% of edetate disodium, about 0.034% of propylparaben, about 0.017% of butylparaben, about 0.35% of xanthan gum, about 0.05% of Poloxamer 407, about 1.25% of sodium phosphate dibasic heptahydrate, about 0.75% of sodium phosphate monobasic monohydrate, about 20% of sucrose, about 10% of sorbitol solution, and about 0.1% of titanium dioxide.

Another particular embodiment of the invention is the aqueous pharmaceutical suspension, buffered to a pH about 5.80 to about 7.00, comprising, by weight/volume (g/100 mL), about 0.60% of fexofenadine zwitterionic dihydrate Form I having a particle size of less than about 40 µm for at least about 90% of the fexofenadine zwitterionic dihydrate Form I, about 2.5% of propylene glycol, about 0.15% of edetate disodium, about 0.034% of propylparaben, about 0.017% of butylparaben, about 0.35% of xanthan gum, about 0.05% of Poloxamer 407, about 1.25% of sodium phosphate dibasic heptahydrate, about 0.75% of sodium phosphate monobasic monohydrate, about 10% of sucrose, about 20% of sorbitol solution, about 0.1% of titanium dioxide, and about 0.4% of raspberry cream flavor.

Another particular embodiment of the invention is the aqueous pharmaceutical suspension comprising, by weight/volume (g/100 mL), about 0.60% of fexofenadine zwitterionic dihydrate Form I, about 2.5% of propylene glycol, about 0.042% of propylparaben, about 0.021% of butylparaben, about 0.35% of xanthan gum, about 0.05% of Poloxamer 407, about 1.25% of sodium phosphate dibasic heptahydrate, about 0.75% of sodium phosphate monobasic monohydrate, about 10% of sucrose, and about 10% of xylitol.

Another particular embodiment of the invention is the aqueous pharmaceutical suspension comprising, by weight/volume (g/100 mL), about 0.60% of fexofenadine zwitterionic dihydrate Form I, about 2.5% of propylene glycol, about 0.042% of propylparaben, about 0.021% of butylparaben, about 0.35% of xanthan gum, about 0.05% of Poloxamer 407, about 1.25% of sodium phosphate dibasic heptahydrate, about 0.75% of sodium phosphate monobasic monohydrate, about 20% of sucrose, and about 10% of xylitol.

It is to be understood that this invention covers all appropriate combinations of the particular embodiments referred thereto.

The suspension formulation according to the present invention is particularly suitable for ease of dosing in children, and in adults having problems with swallowing capsules and tablets.

The suspension agent used in this invention enhances physical stability of the product by sufficiently increasing the viscosity so as to retard the setting rate, yet allowing adequate pourability. Additionally, the suspending agent system allows the product to be easily resuspendable, thus an appropriate dose can be delivered with minimal shaking. The viscosity of the product allows the active agent to remain uniformly suspended after administration of the dose.

The aqueous pharmaceutical suspensions of the invention can be prepared by adding a dispersion of the suspending agent and pre-dissolved components of the preservative system in a suitable co-solvent to an aliquot of water, previously heated at approximately 25-80° C., particularly 35-80° C., more particularly 35-45° C. The addition of the dispersion using this method promotes hydration and dissolution of the suspending agent. The temperature is maintained through the subsequent addition of a portion of the buffer system (to maintain pH control), the remaining component of the preservative system and the components of the sweetener system, resulting in the formation of a bulk solution.

The active agent is dispersed in an aqueous solution of the remaining components of the buffer system and the wetting agent. The pH of the solution is controlled prior to addition of the active agent to maintain the appropriate physical form. If added, the opacifying agent is subsequently added and the active dispersion is added to the aforementioned bulk solution previously cooled to 20-35° C., particularly 20-30° C., resulting in the formation of a suspension. The flavoring agent and remaining water, if necessary, are added to the desired weight. The bulk suspension is subsequently milled and deaerated. The suspension can be prepared by conventional processing equipment. Alternatively, a high shear mixer such as ADMIX® is used for dispersion of fexofenadine hydrochloride and the preservative/suspending agent mixture, an URSCHEL® are used for milling, and a VERSATOR® is used for deaeration.

The aqueous pharmaceutical suspension of the invention is characterized by the following analytical methods. It should be understood, however, that not all such information is required for one skilled in the art to determine that fexofenadine zwitterionic dihydrate Form I is present in a given composition, but that the determination of the presence of fexofenadine zwitterionic dihydrate Form I can be achieved using any portion of the characterizing information that one skilled in the art would recognize as sufficient for establishing its presence.

$^{13}$C Solid-State Nuclear Magnetic Resonance (SSNMR) Spectrometry

The NMR spectrometer is operated at a $^1$H frequency of 399.870 MHz ($^{13}$C=100.557 MHz) (9.4 Tesla Oxford narrow bore magnet). The main console controlling pulse sequence generation, frequency generation, detection and temperature control is a Varian Unity plus console interfaced to a Sun Microsystems Ultra 10 workstation, running Varian VNMR 6.1C software. Spinning speed control is performed using a HIMS computer systems x86 computer, running Varian MAS controller software Version 1.0 (9/93) through an interface with the pneumatics control box, with an accuracy of ±1 Hz. A Varian 7 mm double resonance (HX) magic-angle spinning (MAS) probe is used. Samples are packed into 7 mm $Si_3N_4$ rotors and sealed with a TORLON® drive tip. High-power amplifiers used are comprised of an American Microwave Technologies (AMT) model 3448 high-power (1 kW) solid-state amplifier for the X channel and a Chemagnetics amplifier system, consisting of a Chemagnetics high-power (500 W) tube amplifier and a Chemagnetics amplifier power supply, for the $^1$H channel. Because of the high powers used in solid-state NMR spectroscopy, a Varian high-power passive preamplifier is also used. To suppress unwanted frequencies from getting to the receiver, a Trilithic 4 element high-power 200 MHz low pass filter on the X-channel and a K & L Microwave 4 element high-power 400 MHz bandpass filter for the proton channel are attached to the associated 50 Ω coaxial cable attached to the probe. Probe circuit tuning is performed using the Varian tuning box attached to the magnet leg. The specified channel is selected and a 50-impedance coaxial cable is connected to the appropriate connector on the probe. The tune and match knobs, on the probe, for the specified channel, are adjusted to lower the reflected power as indicated on the LCD screen. A value of <10 at an attenuation setting of 8 is considered acceptable.

Sample Preparation for SSNMR

Isolation of the solid from the suspension formulation for SSNMR analysis is carried out using a Beckman L8-80 M Ultracentrifuge. The suspension formulation sample is poured into the 40 mL centrifuge tubes and sealed with a cap and o-ring. All tubes are filled with the same amount and placed in the ultracentrifuge rotor, either completely filling the 12-position rotor or evenly spacing out the samples to balance the rotor during the centrifugation. The samples are spun at 35000 revolutions per minute (RPM) for 45 minutes, at a temperature of 20° C., and with a vacuum setting of 1 micron. Upon completion of the centrifugation, the tubes are removed, the solution is poured off, and the tubes are inverted over a piece of filter paper for approximately 1 hour, changing position on the filter paper intermittently, since the remaining solution in the tube is not absorbed into the filter paper. The tubes are sealed with a cap and placed in either a 5° C. refrigerator or a −20° C. freezer, until the analysis is performed. If necessary, the samples are placed in a 50° C. oven for approximately 20 hours, prior to being placed in the refrigerator. Each centrifuge tube is distinctly labeled, and the resulting solid is assigned a unique lot number. The samples are maintained at low temperature storage until approximately 5 minutes prior to analysis.

X-Ray Powder Diffraction (XRPD)

XRPD patterns are obtained on either a Scintag X2 or XDS 2000 θ/θ diffractometer operating with copper radiation at 45 kV and 40 mA, using either a Thermo ARL Peltier-cooled solid-state detector or a Moxtek Peltier air-cooled detector respectively. Source slits of 2 and 4 mm and detector slits of 0.5 and 0.3 mm are used for data collection. Samples that are recrystallized and slurried are gently milled using a mortar and pestle. Samples are placed in a stainless steel sample holder, leveled using a glass microscope slide, and scanned on either a single position stage or a six-position auto-sampler. XRPD patterns of the samples are obtained from 2° to 42° 2θ at 1 °/min. Calibration of both diffractometers is verified annually using a silicon powder standard. Raw data files are converted to ASC II format, transferred to an IBM compatible computer, and displayed in ORIGIN® 6.1 for Windows.

Fourier Transform Infrared (FTIR) Spectometry

FTIR spectra are collected on a BioRad FTIR Model FTS6000, using a BioRad diffuse reflectance apparatus, Model: DR. The sample spectrum for all analyses is defined by 16 scans at 2 cm$^{-1}$ resolution and 64 scans per background. Samples for analysis are prepared by milling a small amount of sample with potassium bromide (KBr), using a mortar and pestle at about a 1:10 ratio. The resulting mixture is then placed in the diffuse reflectance sample holder, which is placed in the spectrometer and allowed to purge with $N_2$ gas for 5 minutes.

Figure 2:
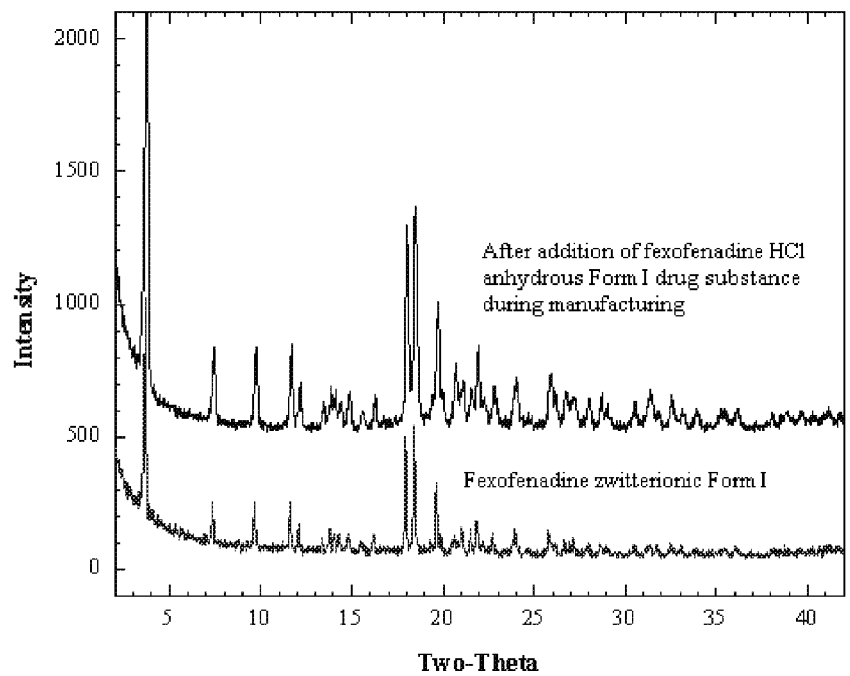
FIG. 2 is X-ray Powder Diffraction pattern of the suspended fexofenadine collected after addition of fexofenadine hydrochloride anhydrous Form I to the buffered solution during the manufacturing process, and fexofenadine zwitterionic dihydrate Form I.
Figure 3:
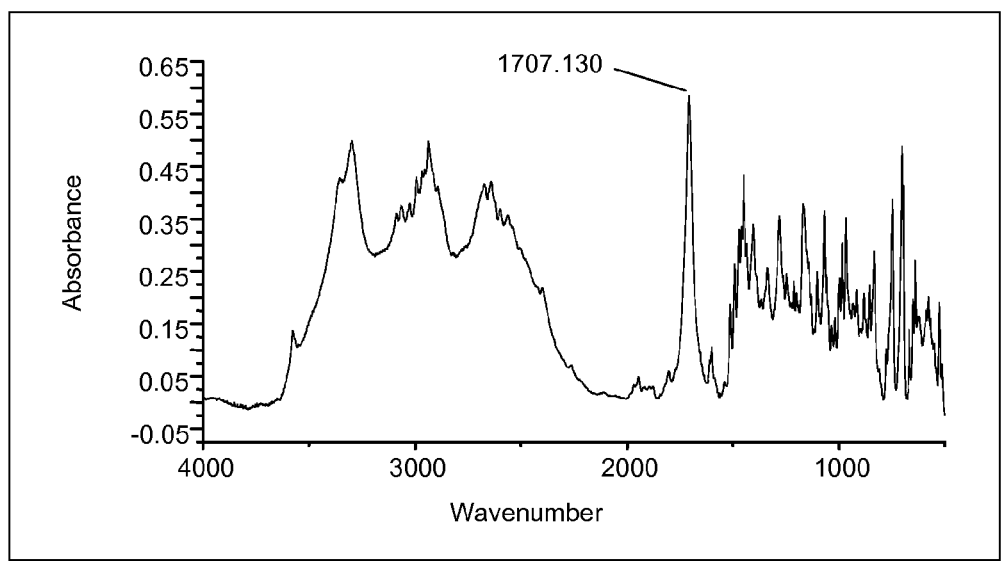
FIG. 3 is a Fourier Transform-Infrared spectrum for fexofenadine hydrochloride anhydrous Form I.
Figure 4:
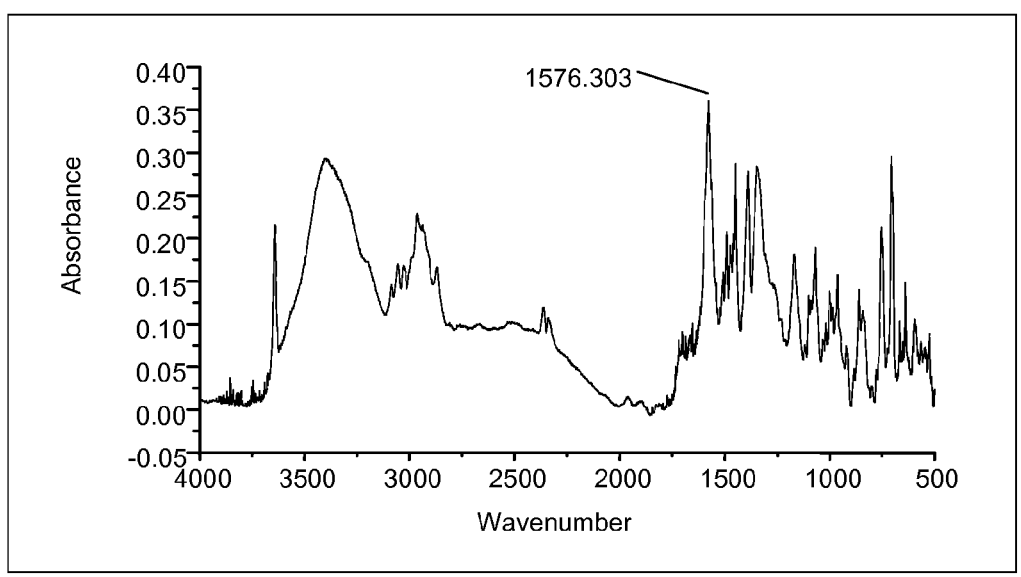
FIG. 4 is a Fourier Transform-Infrared spectrum for fexofenadine zwitterionic dihydrate Form I.

Fexofenadine is amphoteric and exists in multiple polymorphic and pseudopolymorphic forms, including hydrochloride, hydrate and solvate forms. Fexofenadine hydrochloride anhydrous Form I is converted to fexofenadine zwitterionic dihydrate Form I during manufacture by controlling the pH. Within the pH range of about 4.25 to about 9.43, particularly about 5.00 to about 8.00, or more particularly about 5.80 to about 7.00, the physical form of fexofenadine exists mostly as the zwitterionic dihydrate Form I. As pH is controlled throughout the manufacturing process, upon addition of the fexofenadine hydrochloride anhydrous Form I to the buffered solution within the aforementioned pH range, its conversion to the fexofenadine zwitterionic dihydrate Form I is confirmed by XRPD and SSNMR evaluation. FIGS. 1 and 2 show SSNMR and XRPD spectra of the suspended fexofenadine respectively, collected during the manufacturing process. An FTIR method is developed to discriminate between the respective physical forms of anhydrous Form I of fexofenadine hydrochloride and the fexofenadine zwitterionic dihydrate Form I for use as a potential release test. Representative spectra of the anhydrous Form I of fexofenadine hydrochloride and the fexofenadine zwitterionic dihydrate Form I are depicted in FIGS. 3 and 4, respectively. The targeted physical form of fexofenadine (the zwitterionic dihydrate Form I) is maintained for a minimum of about 18 months; more particularly for about 24 months.

The following examples are provided to illustrate the invention and are not intended to be limiting thereof:

EXAMPLES

Example 1

Propylparaben (3.06 kg) and butylparaben (1.53 kg) are added to a suitably sized stainless steel vessel containing approximately 198.2 kg of propylene glycol and dissolved with a high shear mixer (i.e., ADMIX® ROTOSOLVER™). Xanthan gum is added slowly to the mixture and uniformly dispersed. With the recirculation loop on, the dispersion is transferred to a jacketed main compounding tank containing approximately 5,488 kg of purified water that is previously heated to 35-45° C., and mixed. The batch is continually mixed through the end of processing. The temperature is maintained to the xylitol addition step. The vessel is rinsed with the remaining propylene glycol (27 kg) and a portion of purified water (approximately 50.3 kg), and the rinse is transferred to the main compounding tank. The edetate disodium (1.351 kg) is added to the jacketed vessel and dissolved. Portions of sodium phosphate dibasic heptahydrate (67.57 kg) and sodium phosphate monobasic monohydrate (41.45 kg) are added to the jacketed vessel and dissolved. Sucrose (1802 kg) and xylitol (901 kg) are added to the vessel and dissolved. The solution in the jacketed vessel is cooled to 20-30° C. The pH of the solution is measured. In a separate vessel, the remaining portions of sodium phosphate dibasic heptahydrate (45.03 kg) and sodium phosphate monobasic monohydrate (26.15 kg) are added to approximately 950 kg of purified water and dissolved with a high shear mixer. Poloxamer 407 (4.5 kg) is added and dissolved. The pH of the solution is measured. Anhydrous Form I of fexofenadine hydrochloride (54.1 kg) is added slowly to the solution and a uniform dispersion is formed. Titanium dioxide (9.01 kg) is added slowly to the dispersion and a uniform dispersion is formed. The dispersion is transferred to the solution in the jacketed main compounding tank. The tank containing the dispersion is rinsed with a portion of purified water (approximately 250 kg) and transferred to the main compounding tank. The raspberry cream flavor is added with a pressure can to the main compounding tank and dissolved. Sufficient purified water is added, if necessary to achieve the target net weight (10,000 kg). Mixing is continued and a uniform suspension is formed. The pH is measured. The suspension is milled (i.e., URSCHEL® milled) and deaerated. The resulting suspension contains 30 mg of fexofenadine zwitterionic dihydrate Form I (converted from anhydrous Form I of fexofenadine hydrochloride) per 5 mL of suspension. The composition is shown in Table 1.

Example 2

Following the general method of Example 1, a suspension containing about 30 mg of fexofenadine zwitterionic dihydrate Form I (converted from anhydrous Form I of fexofenadine hydrochloride) per 5 mL of suspension and having the composition as described in Table 1 is prepared. In this preparation, the level of sucrose is reduced from about 20% to about 10% weight/volume (g/100 mL).

Example 3

Following the general method of Example 1, a suspension containing about 30 mg of fexofenadine zwitterionic dihydrate Form I (converted from anhydrous Form I of fexofenadine hydrochloride) per 5 mL of suspension and having the composition as described in Table 1 is prepared. In this preparation, the sorbitol solution noncrystallizing NF, is substituted for xylitol at a level of about 10% weight/volume (g/100 mL).

Examples 4-9

Following the general method of Example 1, fexofenadine suspensions having the compositions as described in Table 1 are prepared.

TABLE 1

| Ingredient (in % w/v) | Examples | | | | | | | | |
|---|---|---|---|---|---|---|---|---|---|
| | 1 | 2 | 3 | 4 | 5 | 6 | 7 | 8 | 9 |
| Fexofenadine zwitterionic dihydrate Form I | 0.6 | 0.6 | 0.6 | 0.6 | 0.6 | 1.2 | 1.2 | 0.6 | 0.6 |
| Propylene Glycol | 2.5 | 2.5 | 2.5 | 2.5 | 2.5 | 2.5 | 2.5 | 2.5 | 2.5 |
| Edetate Disodium | 0.15 | 0.15 | 0.15 | — | — | — | — | — | — |
| Propylparaben | 0.034 | 0.034 | 0.034 | 0.030 | 0.030 | 0.030 | 0.030 | 0.042 | 0.042 |
| Butylparaben | 0.017 | 0.017 | 0.017 | 0.015 | 0.015 | 0.015 | 0.015 | 0.021 | 0.021 |
| Xanthan Gum | 0.35 | 0.35 | 0.35 | 0.35 | 0.35 | 0.35 | 0.35 | 0.35 | 0.35 |
| Poloxamer 407 | 0.05 | 0.05 | 0.05 | 0.05 | 0.05 | 0.05 | 0.05 | 0.05 | 0.05 |
| Titanium Dioxide | 0.1 | 0.1 | 0.1 | 0.1 | 0.1 | 0.1 | 0.1 | 0.1 | 0.1 |
| Sodium Phosphate Dibasic Heptahydrate | 1.25 | 1.25 | 1.25 | 1.25 | 1.25 | 1.25 | 1.25 | 1.25 | 1.25 |
| Sodium Phosphate Monobasic Monohydrate | 0.75 | 0.75 | 0.75 | 0.75 | 0.75 | 0.75 | 0.75 | 0.75 | 0.75 |
| Sucrose | 20 | 10 | 20 | 40 | 40 | 40 | — | 20 | 10 |
| Xylitol | 10 | 10 | — | — | — | — | 40 | 10 | 10 |
| Sorbitol Solution, Noncrystallizing NF | — | — | 10 | — | — | — | 10 | — | — |
| Saccharin Sodium | — | — | — | — | — | — | 0.05 | — | — |
| PEG 400 | — | — | — | 1.00 | — | 1.00 | 1.00 | — | — |
| Raspberry Cream Flavor | 0.4 | 0.4 | 0.4 | 0.4 | 0.4 | 0.4 | 0.4 | 0.4 | 0.4 |
| pH | 6.2 | 6.2 | 6.2 | 6.2 | 6.2 | 6.2 | 6.2 | 6.2 | 6.2 |

Bioavailability Study

Study 1:

A two-way crossover, randomized and open label bioequivlalence study comparing the fexofenadine suspension of Example 1 to the marketed 30 mg fexofenadine HCl (ALLEGRA®) tablet in fifty-three healthy adult subjects under fasted conditions is conducted. The assessment of bioequivalence of 5 mL of fexofenadine suspension of Example 1 relative to 30 mg marketed ALLEGRA® tablet is conducted after excluding four subjects whose concentrations are deviant from Standard Operating Procedure. The results of the study are shown in Table 2 below.

TABLE 2

| Parameter | Treatment [1] | No. of Subject | Arithmetic Mean (CV %) | Geometric LS Mean | Treatment Comparison | |
|---|---|---|---|---|---|---|
| | | | | | Ratio [2] | 90% CI |
| AUC(0-∞) (ng · h/mL) | Tablet | 49 | 732 (44.5) | 665 | 97.5 | 87.7-109 |
| | Suspension | 49 | 714 (47.5) | 649 | | |
| Cmax (ng/mL) | Tablet | 49 | 109 (55.0) | 95.5 | 109 | 96.1-122 |
| | Suspension | 49 | 118 (56.2) | 104 | | |

[1]: Tablet: a single oral dose of 30 mg fexofenadine HCl as marketed tablet (reference).

Suspension: a single oral dose of 5 mL of the fexofenadine suspension of Example 1 (test).

[2]: Ratio = geometric LS mean test/geometric LS mean reference (Suspension/Tablet).

Study 2:

A complete crossover, randomized and open label pilot bioavailability study comparing the fexofenadine suspensions of Examples 4, 5, 6 and 7 to the marketed 60 mg fexofenadine HCl (ALLEGRA®) tablet in thirty-six healthy adult subjects under fasted condition is conducted. The results of the study are shown in Table 3 below. The data for AUC(0-∞) and Cmax are presented as mean values ±standard deviation (SD).

TABLE 3

| Parameter | Treatment [3] | | | | |
|---|---|---|---|---|---|
| | A | B | C | D | E |
| AUC(0-∞) (ng · h/mL) | 1595 ± 779 | 1250 ± 531 | 1518 ± 563 | 1150 ± 699 | 1153 ± 396 |
| Cmax (ng/mL) | 340.2 ± 198.7 | 220.1 ± 112.2 | 287.3 ± 124.6 | 150.5 ± 62.5 | 168.1 ± 74.9 |
| 90% CI [4] AUC(0-∞) | 140.29% (114.13-172.44) | 112.83% (91.79-138.68) | 122.68% (99.81-150.79) | 88.68% (72.15-109.00) | |
| 90% CI [4] Cmax | 213.92% (172.88-264.69) | 143.53% (116.00-177.60) | 151.19% (122.19-187.07 | 79.73 (64.44-98.66) | |

[3]: Treatment A: a single oral dose of 10 mL fexofenadine suspension of Example 4 (test).
Treatment B: a single oral dose of 10 mL fexofenadine suspension of Example 5 (test).
Treatment C: a single oral dose of 5 mL fexofenadine suspension of Example 6 (test).
Treatment D: a single oral dose of 5 mL fexofenadine suspension of Example 7 (test).
Treatment E: a single oral dose of 60 mg fexofenadine HCl as marketed tablet (reference).
[4]: Relative to Treatment E.

Study 3:

A complete crossover, randomized and open label pilot bioavailability study comparing the fexofenadine suspensions of Examples 8 and 9 to the marketed 60 mg fexofenadine HCl(ALLEGRA®) tablet in twenty-two healthy adult subjects under fasted condition is conducted. The results of the study are shown in Table 4 below.

TABLE 4

| Parameter | Treatment [5] | No. of Subject | Arithmetic Mean (CV %) | Geometric LS Mean | Treatment Comparison | |
|---|---|---|---|---|---|---|
| | | | | | Ratio [6] | 90% CI |
| AUC(0-∞) (ng · h/mL) | F | 22 | 1393.4 (30.2) | 1321.9 | | |
| | G | 22 | 1413.1 (45.7) | 1304.7 | 98.69 | 85.47-113.96 |
| | H | 22 | 1461.3 (38.3) | 1368.3 | 103.51 | 89.55-119.64 |
| Cmax (ng/mL) | F | 22 | 210.12 (39.9) | 193.67 | | |
| | G | 22 | 244.90 (58.6) | 212.39 | 109.67 | 89.39-134.54 |
| | H | 22 | 261.17 (48.9) | 233.63 | 120.64 | 98.18-148.23 |

[5]: Treatment F: a single oral dose of 60 mg fexofenadine HCl as marketed tablet administered with 240 mL room temperature water (reference).
Treatment G: a single oral dose of 10 mL fexofenadine suspension of Example 8 with 230 mL room temperature water (test).
Treatment H: a single oral dose of 10 mL fexofenadine suspension of Example 9 with 230 mL room temperature water (test).
[6]: Ratio = geometric LS mean test/geometric LS mean reference.

The present invention may be embodied in other specific forms without departing from the spirit or essential attributes thereof.

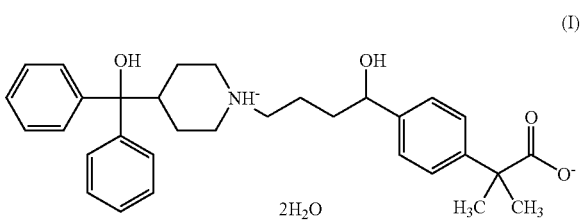

(I)

We claim:

1. An aqueous pharmaceutical suspension, having a pH 5.8 to 7.0 adjusted by a buffer system, comprising, by weight/volume (g/100 mL),
0.03% to 4.80% of fexofenadine zwitterionic dihydrate Form I of formula (I) having a particle size of less than 280 μm for at least 90% of the fexofenadine zwitterionic dihydrate Form I;
0.01% to 0.20% of a wetting agent;
a suspending agent selected from 0.10% to 0.50% of a hydrocolloid gum, or 0.1% to 1.0% of hydroxyethylcellulose;

a sweetener system comprising
  5% to 40% of sucrose or invert sucrose; and
  5% to 40% of xylitol, sorbitol or sorbitol solution, or maltitol solution;
  provided that the ratio of the amount of (sucrose or invert sucrose) : (xylitol, sorbitol or sorbitol solution, or maltitol solution) is 1:1 to 2:1; and
a preservative system comprising
  0.010% to 0.058% of propylparaben, sodium propylparaben or potassium propylparaben;
  0.0005% to 0.0350% of butylparaben or sodium butylparaben; and
  0.06% to 0.26% of edetate disodium, 0.01% to 0.27% of benzoic acid or sodium benzoate, 0.01% to 0.30% of sorbic acid or potassium sorbate or 0.10% to 1.50% of benzyl alcohol.

2. The aqueous pharmaceutical suspension according to claim 1, wherein the particle size is less than 50 μm for at least 90% of the fexofenadine zwitterionic dihydrate Form I.

3. The aqueous pharmaceutical suspension according to claim 1, wherein the particle size is less than 40 μm for at least 90% of the fexofenadine zwitterionic dihydrate Form I.

4. The aqueous pharmaceutical suspension according to claim 3, wherein the fexofenadine zwitterionic dihydrate Form I is, by weight/volume (g/100 mL), 0.6% to 1.2%.

5. The aqueous pharmaceutical suspension according to claim 3, wherein the fexofenadine zwitterionic dihydrate Form I is, by weight/volume (g/100 mL), 0.6%.

6. The aqueous pharmaceutical suspension according to claim 3, wherein the wetting agent is, by weight/volume (g/100 mL), 0.01% to 0.05%.

7. The aqueous pharmaceutical suspension according to claim 3, wherein the wetting agent is, by weight/volume (g/100 mL), 0.02% to 0.05%.

8. The aqueous pharmaceutical suspension according to claim 3, wherein the hydrocolloid gum is, by weight/volume (g/100 mL), 0.23% to 0.45%.

9. The aqueous pharmaceutical suspension according to claim 3, wherein the hydrocolloid gum is, by weight/volume (g/100 mL), 0.35% to 0.45%.

10. The aqueous pharmaceutical suspension according to claim 3, wherein the hydrocolloid gum is xanthan gum.

11. The aqueous pharmaceutical suspension according to claim 3, wherein the hydroxyethylcellulose is, by weight/volume (g/100 mL), 0.2% to 0.4%.

12. The aqueous pharmaceutical suspension according to claim 3, wherein the hydroxyethylcellulose is, by weight/volume (g/100 mL), 0.2% to 0.3%.

13. The aqueous pharmaceutical suspension according to claim 3, wherein the xylitol, sorbitol or sorbitol solution, or maltitol solution is, by weight/volume (g/100 mL), 5% to 20%.

14. The aqueous pharmaceutical suspension according to claim 3, wherein the xylitol, sorbitol or sorbitol solution, or maltitol solution is, by weight/volume (g/100 mL), 10% to 20%.

15. The aqueous pharmaceutical suspension according to claim 3, wherein the xylitol, sorbitol or sorbitol solution, or maltitol solution is, by weight/volume (g/100 mL), 10%.

16. The aqueous pharmaceutical suspension according to claim 3, wherein the sucrose or invert sucrose is, by weight/volume (g/100 mL), 10% to 40%.

17. The aqueous pharmaceutical suspension according to claim 3, wherein the sucrose or invert sucrose is, by weight/volume (g/100 mL), 10% to 20%.

18. The aqueous pharmaceutical suspension according to claim 3, wherein the sucrose or invert sucrose is, by weight/volume (g/100 mL), 20%.

19. The aqueous pharmaceutical suspension according to claim 3, wherein the sweetener system comprises xylitol and sucrose.

20. The aqueous pharmaceutical suspension according to claim 3, wherein the sweetener system comprises xylitol and sucrose, and the ratio of the amount of sucrose : xylitol is 2:1.

21. The aqueous pharmaceutical suspension according to claim 3, wherein the sweetener system comprises, by weight/volume (g/100 mL), 0% to 20% of xylitol, and 10% to 40% of sucrose.

22. The aqueous pharmaceutical suspension according to claim 3, wherein the sweetener system comprises, by weight/volume (g/100 mL), 10% to 20% of xylitol, and 10% to 20% of sucrose.

23. The aqueous pharmaceutical suspension according to claim 3, wherein the sweetener system comprises, by weight/volume (g/100 mL), 20% of sucrose and 10% of xylitol.

24. The aqueous pharmaceutical suspension according to claim 3, the ratio of the amount of (sucrose or invert sucrose): (xylitol, sorbitol or sorbitol solution, or maltitol solution) is 2:1.

25. The aqueous pharmaceutical suspension according to claim 3, wherein the propylparaben, sodium propylparaben, or potassium propylparaben is, by weight/volume (g/100 mL), 0.014% to 0.048%.

26. The aqueous pharmaceutical suspension according to claim 3, wherein the propylparaben, sodium propylparaben, or potassium propylparaben is, by weight/volume (g/100 mL), 0.027% to 0.040%.

27. The aqueous pharmaceutical suspension according to claim 3, wherein the butylparaben, or sodium butylparaben is, by weight/volume (g/100 mL), 0.0008% to 0.0240%.

28. The aqueous pharmaceutical suspension according to claim 3, wherein the butylparaben, or sodium butylparaben is, by weight/volume (g/100 mL), 0.014% to 0.020%.

29. The aqueous pharmaceutical suspension according to claim 3, wherein the edetate disodium is, by weight/volume (g/100 mL), 0.10% to 0.18%.

30. The aqueous pharmaceutical suspension according to claim 3, wherein the edetate disodium is, by weight/volume (g/100 mL), 0.12% to 0.18%.

31. The aqueous pharmaceutical suspension according to claim 3, wherein the preservative system comprises propylparaben, butylparaben and edetate disodium.

32. The aqueous pharmaceutical suspension according to claim 3, wherein the benzoic acid or sodium benzoate is, by weight/volume (g/100 mL), 0.10% to 0.20%.

33. The aqueous pharmaceutical suspension according to claim 3, wherein the benzoic acid or sodium benzoate is, by weight/volume (g/100 mL), 0.12% to 0.18%.

34. The aqueous pharmaceutical suspension according to claim 3, wherein the sorbic acid or potassium sorbate is, by weight/volume (g/100 mL), 0.10% to 0.22%.

35. The aqueous pharmaceutical suspension according to claim 3, wherein the sorbic acid or potassium sorbate is, by weight/volume (g/100 mL), 0.12% to 0.20%.

36. The aqueous pharmaceutical suspension according to claim 3, wherein the benzyl alcohol is, by weight/volume (g/100 mL), 0.25% to 1.00%.

37. The aqueous pharmaceutical suspension according to claim 3, wherein the benzyl alcohol is, by weight/volume (g/100 mL), 0.24% to 0.50%.

38. The aqueous pharmaceutical suspension according to claim 3, wherein the buffering uses a buffer system comprising, by weight/volume (g/100 mL),
   0.75% of sodium phosphate monobasic or a corresponding equivalent amount of a sodium phosphate monobasic hydrate, or 0.89% of potassium phosphate monobasic; and
   1.25% of sodium phosphate dibasic or a corresponding equivalent amount of a sodium phosphate dibasic hydrate, or 1.86% of potassium phosphate dibasic or a corresponding equivalent amount of a potassium phosphate dibasic hydrate.

39. The aqueous pharmaceutical suspension according to claim 6, wherein the buffering uses a buffer system comprising, by weight/volume (g/100 mL),
   0.75% of sodium phosphate monobasic or a corresponding equivalent amount of a sodium phosphate monobasic hydrate; and
   1.25% of sodium phosphate dibasic or a corresponding equivalent amount of a sodium phosphate dibasic hydrate.

40. The aqueous pharmaceutical suspension according to claim 3, wherein the wetting agent is nonionic.

41. The aqueous pharmaceutical suspension according to claim 3, wherein the wetting agent is Poloxamer 407 or Poloxamer 188.

42. The aqueous pharmaceutical suspension according to claim 3, wherein the wetting agent is Poloxamer 407.

43. The aqueous pharmaceutical suspension according to claim 3, further comprising, by weight/volume (g/100 mL), 0.1% to 3.0% of microcrystalline cellulose.

44. The aqueous pharmaceutical suspension according to claim 3, further comprising, by weight/volume (g/100 mL), 1.0% to 2.0% of microcrystalline cellulose.

45. The aqueous pharmaceutical suspension according to claim 3, further comprising, by weight/volume (g/100 mL), 1.5% to 2.0% of microcrystalline cellulose.

46. The aqueous pharmaceutical suspension according to claim 3, further comprising, by weight/volume (g/100 mL), 0.01% to 0.20% of saccharin.

47. The aqueous pharmaceutical suspension according to claim 3, further comprising, by weight/volume (g/100 mL), 0.012% to 0.130% of saccharin.

48. The aqueous pharmaceutical suspension according to claim 3, further comprising, by weight/volume (g/100 mL), 0.05% to 0.10% of saccharin.

49. The aqueous pharmaceutical suspension according to claim 3, further comprising, by weight/volume (g/100 mL), 0.01% to 1.00% of acesulfame potassium or sucralose.

50. The aqueous pharmaceutical suspension according to claim 3, further comprising, by weight/volume (g/100 mL), 0.01% to 0.50% of acesulfame potassium or sucralose.

51. The aqueous pharmaceutical suspension according to claim 3, further comprising, by weight/volume (g/100 mL), 0.01% to 0.10% of acesulfame potassium or sucralose.

52. The aqueous pharmaceutical suspension according to claim 3, further comprising, by weight/volume (g/100 mL), 0.1% to 15.0% of propylene glycol.

53. The aqueous pharmaceutical suspension according to claim 3, further comprising, by weight/volume (g/100 mL), 1.0% to 10.0% of propylene glycol.

54. The aqueous pharmaceutical suspension according to claim 3, further comprising, by weight/volume (g/100 mL), 2.5% to 5.0% of propylene glycol.

55. The aqueous pharmaceutical suspension according to claim 3, further comprising, by weight/volume (g/100 mL), 0% to 4% of polyethylene glycol 200, polyethylene glycol 300 or polyethylene glycol 400.

56. The aqueous pharmaceutical suspension according to claim 3, further comprising, by weight/volume (g/100 mL), 0% to 2% of polyethylene glycol 200, polyethylene glycol 300 or polyethylene glycol 400.

57. The aqueous pharmaceutical suspension according to claim 3, further comprising, by weight/volume (g/100 mL), 0% to 1% of polyethylene glycol 200, polyethylene glycol 300 or polyethylene glycol 400.

58. The aqueous pharmaceutical suspension according to claim 3, further comprising, by weight/volume (g/100 mL), 0% to 0.50% of an opacifying agent.

59. The aqueous pharmaceutical suspension according to claim 3, further comprising, by weight/volume (g/100 mL), 0% to 0.10% of an opacifying agent.

60. The aqueous pharmaceutical suspension according to claim 3, further comprising, by weight/volume (g/100 mL), 0.05% to 0.10% of an opacifying agent.

61. The aqueous pharmaceutical suspension according to claim 58, wherein the opacifying agent is titanium dioxide.

62. The aqueous pharmaceutical suspension according to claim 59, wherein the opacifying agent is titanium dioxide.

63. The aqueous pharmaceutical suspension according to claim 60, wherein the opacifying agent is Titanium dioxide.

64. The aqueous pharmaceutical suspension according to claim 3, further comprising, by weight/volume (g/100 mL), 0.20% to 0.70% of a flavoring agent.

65. The aqueous pharmaceutical suspension according to claim 3, further comprising, by weight/volume (g/100 mL), 0.30% to 0.45% of a flavoring agent.

66. The aqueous pharmaceutical suspension according to claim 3, further comprising, by weight/volume (g/100 mL), 0.40% to 0.45% of a flavoring agent.

67. The aqueous pharmaceutical suspension according to claim 66, wherein the flavoring agent is artificial raspberry cream flavor or artificial orange cream flavor.

68. The aqueous pharmaceutical suspension according to claim 67, wherein the flavoring agent is artificial raspberry cream flavor or artificial orange cream flavor.

69. The aqueous pharmaceutical suspension according to claim 68, wherein the flavoring agent is artificial raspberry cream flavor or artificial orange cream flavor.

70. The aqueous pharmaceutical suspension according to claim 3, comprising, by weight/volume (g/100 mL), 0.60% of fexofenadine zwitterionic dihydrate Form I, 2.5% of propylene glycol, 0.15% of edetate disodium, 0.034% of propylparaben, 0.017% of butylparaben, 0.35% of xanthan gum, 0.05% of Poloxamer 407, 1.25% of sodium phosphate dibasic heptahydrate, 0.75% of sodium phosphate monobasic monohydrate, 20% of sucrose, and 10% of xylitol.

71. The aqueous pharmaceutical suspension according to claim 70, further comprising, by weight/volume (g/100 mL), 0.1% of titanium dioxide.

72. The aqueous pharmaceutical suspension according to claim 71, further comprising, by weight/volume (g/100 mL), 0.4% of raspberry cream flavor.

73. The aqueous pharmaceutical suspension according to claim 3, comprising, by weight/volume (g/100 mL), 0.60% of fexofenadine zwitterionic dihydrate Form I, 2.5% of propylene glycol, 0.15% of edetate disodium, 0.034% of propylparaben, 0.017% of butylparaben, 0.35% of xanthan gum, 0.05% of Poloxamer 407, 1.25% of sodium phosphate dibasic heptahydrate, 0.75% of sodium phosphate monobasic monohydrate, 10% of sucrose, and 10% of xylitol.

74. The aqueous pharmaceutical suspension according to claim 73, further comprising, by weight/volume (g/100 mL), 0.1% of titanium dioxide.

75. The aqueous pharmaceutical suspension according to claim 74, further comprising, by weight/volume (g/100 mL), 0.4% of raspberry cream flavor.

76. The aqueous pharmaceutical suspension according to claim 3, comprising, by weight/volume (g/100 mL), 0.60% of fexofenadine zwitterionic dihydrate Form I, 2.5% of propylene glycol, 0.15% of edetate disodium, 0.034% of propylparaben, 0.017% of butylparaben, 0.35% of xanthan gum, 0.05% of Poloxamer 407, 1.25% of sodium phosphate dibasic heptahydrate, 0.75% of sodium phosphate monobasic monohydrate, 20% of sucrose, and 10% of sorbitol solution.

77. The aqueous pharmaceutical suspension according to claim 76, further comprising, by weight/volume (g/100 mL), 0.1% of titanium dioxide.

78. The aqueous pharmaceutical suspension according to claim 77, further comprising, by weight/volume (g/100 mL), 0.4% of raspberry cream flavor.

79. The aqueous pharmaceutical suspension according to claim 4, comprising, by weight/volume (g/100 mL), 0.60% of fexofenadine zwitterionic dihydrate Form I, 2.5% of propylene glycol, 0.15% of edetate disodium, 0.034% of propylparaben 0.017% of butylparaben, 0.35% of xanthan gum, 0.05% of Poloxamer 407, 1.25% of sodium phosphate dibasic heptahydrate, 0.75% of sodium phosphate monobasic monohydrate, 20% of sucrose, and 10% of sorbitol solution.

80. The aqueous pharmaceutical suspension according to claim 79, further comprising, by weight/volume (g/100 mL), 0.1% of titanium dioxide.

81. The aqueous pharmaceutical suspension according to claim 80, further comprising, by weight/volume (g/100 mL), 0.4% of raspberry cream flavor.

82. The aqueous pharmaceutical suspension according to claim 1, comprising, by weight/volume (g/100 mL), 0.60% of fexofenadine zwitterionic dihydrate Form I, 2.5% of propylene glycol, 0.042% of propylparaben 0.021% of butylparaben, 0.35% of xanthan gum, 0.05% of Poloxamer 407, 1.25% of sodium phosphate dibasic heptahydrate, 0.75% of sodium phosphate monobasic monohydrate, 10% of sucrose, and 10% of xylitol.

83. The aqueous pharmaceutical suspension according to claim 1, comprising, by weight/volume (g/100 mL), 0.60% of fexofenadine zwitterionic dihydrate Form I, 2.5% of propylene glycol, 0.042% of propylparaben 0.021% of butylparaben, 0.35% of xanthan gum, 0.05% of Poloxamer 407, 1.25% of sodium phosphate dibasic heptahydrate, 0.75% of sodium phosphate monobasic monohydrate, 20% of sucrose, and 10% of xylitol.

84. The aqueous pharmaceutical suspension according to claim 1, wherein the sweetener system comprises, by weight/volume (g/100 mL), 10% to 40% sucrose; and 20% xylitol.

85. The aqueous pharmaceutical suspension according to claim 1, wherein the sweetener system comprises, by weight/volume (g/100 mL), 10% to 20% sucrose, and 10% to 20% xylitol.

86. An aqueous pharmaceutical suspension, having a pH 5.8 to 7.0 adjusted by a buffer system, wherein the suspension comprises, by weight/volume (g/100 mL),
0.60% of fexofenadine zwitterionic dihydrate Form I of formula (I) having a particle size of less than 40 μm for at least 90% of the fexofenadine zwitterionic dihydrate Form I;

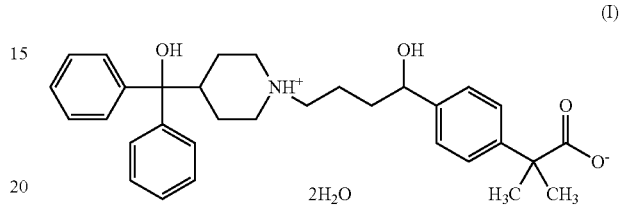

(I)

0.01% to 0.20% of a wetting agent;
a suspending agent selected from 0.10% to 0.50% of a hydrocolloid gum, or 0.1% to 1.0% of hydroxyethylcellulose;
a sweetener system comprising
  10% to 40% of sucrose or invert sucrose; and
  10% to 20% of xylitol, sorbitol or sorbitol solution, or maltitol solution;
  provided that the ratio of the amount of (sucrose or invert sucrose):(xylitol, sorbitol or sorbitol solution, or maltitol solution) is 1:1 to 2:1; and
a preservative system comprising
  0.010% to 0.058% of propylparaben, sodium propylparaben or potassium propylparaben;
  0.0005% to 0.0350% of butylparaben or sodium butylparaben; and
  0.06% to 0.26% of edetate disodium, 0.01% to 0.27% of benzoic acid or sodium benzoate, 0.01% to 0.30% of sorbic acid or potassium sorbate or 0.10% to 1.50% of benzyl alcohol.

87. The aqueous pharmaceutical suspension according to claim 86, comprising, by weight/volume (g/100 mL), 2.5% of propylene glycol; 0.05% of Poloxamer 407; 0.35% of xanthan gum; 10% to 20% of sucrose; 10% of xylitol or sorbitol; 0.034% of propylparaben; 0.017% of butylparaben; 0.15% of edetate disodium; and wherein the buffer system comprises, by weight/volume (g/100 mL), 1.25% of sodium phosphate dibasic heptahydrate and 0.75% of sodium phosphate monobasic monohydrate.

88. The aqueous pharmaceutical suspension according to claim 86, comprising, by weight/volume (g/100 mL), 20% of sucrose and 10% of xylitol.

* * * * *

UNITED STATES PATENT AND TRADEMARK OFFICE
CERTIFICATE OF CORRECTION

PATENT NO. : 8,933,097 B2
APPLICATION NO. : 12/138468
DATED : January 13, 2015
INVENTOR(S) : Kazimierz Chrzan et al.

It is certified that error appears in the above-identified patent and that said Letters Patent is hereby corrected as shown below:

In the Claims:

At column 16, claim number 1, line 55, in the figure of Form I: please replace the negative charge "NH⁻" on the NH group with a positive change --NH$^+$-- as indicated below:

Replace: " 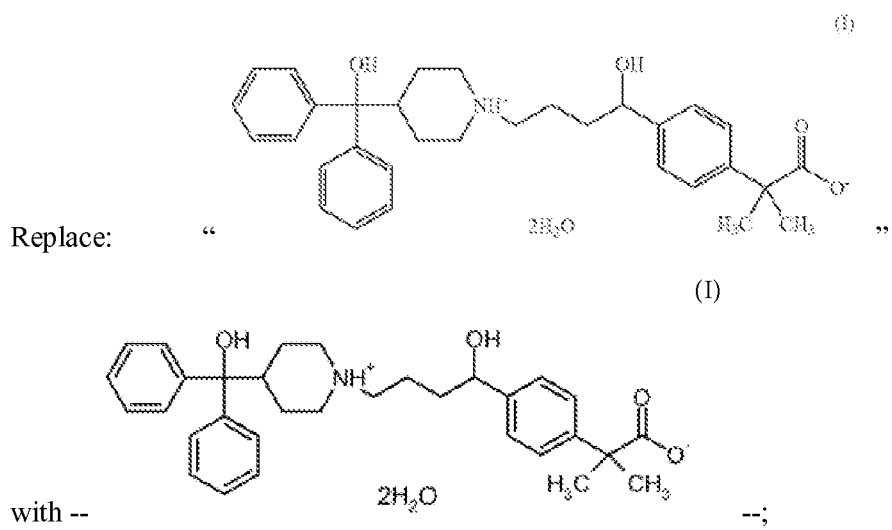 ";

with -- (I) --;

At column 19, claim number 39, line 14: please replace "claim 6, wherein the buffering" with --claim 3, wherein the buffering--;

At column 20, claim number 68, line 41: please replace "claim 67, wherein the" with --claim 65, wherein the--;

Signed and Sealed this
Seventeenth Day of November, 2015

Michelle K. Lee
*Director of the United States Patent and Trademark Office*

CERTIFICATE OF CORRECTION (continued)
U.S. Pat. No. 8,933,097 B2

At column 20, claim number 69, line 44: please replace "claim 68, wherein the" with --claim 64, wherein the--;

At column 21, claim number 83, line 47: please replace "0.042% of propylparaben 0.021% of butylpara-" with --0.042% of propylparaben, 0.021% of butylpara- --.

UNITED STATES PATENT AND TRADEMARK OFFICE
CERTIFICATE OF CORRECTION

| | |
|---|---|
| PATENT NO. | : 8,933,097 B2 |
| APPLICATION NO. | : 12/138468 |
| DATED | : January 13, 2015 |
| INVENTOR(S) | : Chrzan et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1329 days.

Signed and Sealed this
Fifteenth Day of March, 2016

Michelle K. Lee
*Director of the United States Patent and Trademark Office*